US011246630B2

(12) United States Patent
Akbarnia et al.

(10) Patent No.: US 11,246,630 B2
(45) Date of Patent: Feb. 15, 2022

(54) FLEXIBLE FASTENING SYSTEM

(71) Applicant: K2M, Inc., Leesburg, VA (US)

(72) Inventors: Behrooz Akbarnia, LaJolla, CA (US); Burt Yaszay, San Diego, CA (US); Brandon Moore, Leesburg, VA (US); Stuart Weikel, Leesburg, VA (US); Clint Boyd, Winchester, VA (US)

(73) Assignee: K2M, Inc., Leesburg, VA (US)

( * ) Notice: Subject to any disclaimer, the term of this patent is extended or adjusted under 35 U.S.C. 154(b) by 202 days.

(21) Appl. No.: 16/592,243

(22) Filed: Oct. 3, 2019

(65) Prior Publication Data

US 2020/0030008 A1 Jan. 30, 2020

Related U.S. Application Data

(63) Continuation of application No. 15/614,880, filed on Jun. 6, 2017, now Pat. No. 10,470,803, which is a continuation of application No. 14/203,820, filed on Mar. 11, 2014, now Pat. No. 9,675,386.

(60) Provisional application No. 61/775,739, filed on Mar. 11, 2013.

(51) Int. Cl.
*A61B 17/70* (2006.01)
*A61B 17/88* (2006.01)

(52) U.S. Cl.
CPC ...... *A61B 17/7053* (2013.01); *A61B 17/8869* (2013.01)

(58) Field of Classification Search
CPC .............. A61B 17/7049; A61B 17/705; A61B 17/7052; A61B 17/7053; A61B 17/8869; A61B 17/7074; A61B 17/7083
USPC .................................................. 606/263–279
See application file for complete search history.

(56) References Cited

U.S. PATENT DOCUMENTS

| | | |
|---|---|---|
| 5,312,410 A | 5/1994 | Miller et al. |
| 5,383,392 A | 1/1995 | Kowalewski et al. |
| 5,449,361 A | 9/1995 | Preissman |
| 5,496,318 A | 3/1996 | Howland et al. |
| 5,683,392 A | 11/1997 | Richelsoph et al. |
| 5,707,372 A | 1/1998 | Errico et al. |

(Continued)

FOREIGN PATENT DOCUMENTS

| | | |
|---|---|---|
| EP | 0649636 A2 | 4/1995 |
| EP | 2052689 A1 | 4/2009 |

(Continued)

OTHER PUBLICATIONS

European Office Action dated Oct. 15, 2018 cited in EP Application 14 158 813.

(Continued)

*Primary Examiner* — Eduardo C Robert
*Assistant Examiner* — Christina Negrellirodriguez
(74) *Attorney, Agent, or Firm* — Lerner, David, Littenberg, Krumholz & Mentlik, LLP

(57) ABSTRACT

A flexible implant system includes a flexible implant, an implant housing, and an implant set screw. The flexible implant is configured to loop around a portion of a bony element. The implant housing includes a housing body defining a rod passage configured to receive an rod. The housing body also defines an implant passage that receives a portion of the flexible implant. The implant set screw engages the flexible implant within the implant passage to fix the flexible implant to the implant housing.

19 Claims, 28 Drawing Sheets

14
100
20
27
26
B
12

(56) References Cited

U.S. PATENT DOCUMENTS

| | | | |
|---|---|---|---|
| 5,733,286 | A | 3/1998 | Errico et al. |
| 6,086,590 | A | 7/2000 | Margulies et al. |
| 6,238,396 | B1 | 5/2001 | Lombardo |
| 6,436,099 | B1 | 8/2002 | Drewry et al. |
| 6,589,243 | B1 | 7/2003 | Viart et al. |
| 7,285,121 | B2 | 10/2007 | Braun et al. |
| 7,344,539 | B2 | 3/2008 | Serhan et al. |
| 7,481,828 | B2 | 1/2009 | Mazda et al. |
| 7,658,582 | B2 | 2/2010 | Doubler et al. |
| 7,717,940 | B2 | 5/2010 | Woods et al. |
| 7,771,430 | B2 | 8/2010 | Jones et al. |
| 7,862,590 | B2 | 1/2011 | Lim et al. |
| 7,909,826 | B2 | 3/2011 | Serhan et al. |
| 7,959,654 | B2 | 6/2011 | Mazda et al. |
| 7,988,694 | B2 | 8/2011 | Barrus et al. |
| RE42,867 | E | 10/2011 | Hammill, Sr. et al. |
| 8,029,513 | B2 | 10/2011 | Konno et al. |
| 8,113,847 | B2 | 2/2012 | Boachie-Adjei |
| 8,162,946 | B2 | 4/2012 | Baccelli et al. |
| 8,162,991 | B2 | 4/2012 | Strauss et al. |
| 8,167,915 | B2 | 5/2012 | Ferree et al. |
| 8,172,843 | B2 | 5/2012 | Baccelli et al. |
| 8,287,576 | B2 | 10/2012 | Barrus |
| 8,308,729 | B2 | 11/2012 | Nunley et al. |
| 8,308,771 | B2 | 11/2012 | Bennett et al. |
| 8,323,294 | B2 | 12/2012 | Mickiewicz et al. |
| 8,337,532 | B1 | 12/2012 | McLean et al. |
| 8,361,122 | B2 | 1/2013 | Barrus et al. |
| 8,372,120 | B2 | 2/2013 | James |
| 8,377,104 | B2 | 2/2013 | Jones et al. |
| 8,403,971 | B2 | 3/2013 | Barrus et al. |
| 8,465,495 | B2 | 6/2013 | Belliard |
| 8,486,110 | B2 | 7/2013 | Fielding et al. |
| 8,506,603 | B2 | 8/2013 | McClintock et al. |
| 8,672,944 | B2 | 3/2014 | Boachie-Adjei et al. |
| 8,696,718 | B2 | 4/2014 | Barrus et al. |
| 8,714,427 | B2 | 5/2014 | McClintock et al. |
| 8,728,083 | B2 | 5/2014 | Baccelli et al. |
| 8,764,756 | B2 | 7/2014 | Jones |
| 8,814,919 | B2 | 8/2014 | Barrus et al. |
| 8,834,474 | B2 | 9/2014 | Jones et al. |
| 8,882,817 | B2 | 11/2014 | Jones et al. |
| 8,926,668 | B2 | 1/2015 | Douget |
| 8,936,625 | B2 | 1/2015 | Larroque-Lahitette et al. |
| 8,945,189 | B2 | 2/2015 | Barrus et al. |
| 8,961,523 | B2 | 2/2015 | Barrus et al. |
| 8,979,898 | B2 | 3/2015 | Ark et al. |
| 9,023,087 | B2 | 5/2015 | Frankel et al. |
| 9,125,703 | B2 | 9/2015 | McClintock et al. |
| 9,173,685 | B2 | 11/2015 | Lindquist et al. |
| 9,247,969 | B2 | 2/2016 | Nunley et al. |
| 9,675,386 | B2 | 6/2017 | Akbarnia et al. |
| 9,770,267 | B2 | 9/2017 | Lindquist et al. |
| 9,770,268 | B2 | 9/2017 | Albert et al. |
| 10,307,186 | B2 | 6/2019 | Schafer et al. |
| 10,667,852 | B2 | 6/2020 | Shoshtaev |
| 2002/0007183 | A1 | 1/2002 | Lee et al. |
| 2002/0116013 | A1 | 8/2002 | Gleason et al. |
| 2002/0143330 | A1 | 10/2002 | Shluzas |
| 2005/0228375 | A1 | 10/2005 | Mazda |
| 2005/0277920 | A1 | 12/2005 | Slivka et al. |
| 2006/0241598 | A1 | 10/2006 | Khalili |
| 2007/0016189 | A1 | 1/2007 | Lake et al. |
| 2007/0016197 | A1 | 1/2007 | Woods et al. |
| 2008/0015588 | A1 | 1/2008 | Hawkes |
| 2008/0177323 | A1 | 7/2008 | Null et al. |
| 2009/0204118 | A1 | 8/2009 | Pratt |
| 2009/0292308 | A1 | 11/2009 | Jones et al. |
| 2009/0292317 | A1 | 11/2009 | Belliard |
| 2009/0326585 | A1 | 12/2009 | Baccelli |
| 2010/0185243 | A1 | 7/2010 | Pasquet et al. |
| 2011/0106185 | A1 | 5/2011 | Gil et al. |
| 2011/0152934 | A1 | 6/2011 | Asaad |
| 2011/0238118 | A1 | 9/2011 | Baccelli et al. |
| 2011/0301644 | A1 | 12/2011 | Belliard |
| 2012/0130373 | A1 | 5/2012 | Larroque-Lahitette |
| 2012/0226316 | A1 | 9/2012 | Dant et al. |
| 2012/0271356 | A1 | 10/2012 | Ramsay et al. |
| 2013/0041410 | A1 * | 2/2013 | Hestad ................. A61B 17/707 606/263 |
| 2014/0094850 | A1 | 4/2014 | Clement et al. |
| 2014/0257397 | A1 | 9/2014 | Akbarnia et al. |
| 2014/0277142 | A1 | 9/2014 | Blain et al. |
| 2014/0316468 | A1 | 10/2014 | Keiser et al. |
| 2015/0320448 | A1 | 11/2015 | Legallois |
| 2016/0058478 | A1 | 3/2016 | Agarwal et al. |
| 2016/0157896 | A1 | 6/2016 | Palmer et al. |
| 2017/0303970 | A1 | 10/2017 | Puryear et al. |
| 2017/0348025 | A1 | 12/2017 | Albert et al. |

FOREIGN PATENT DOCUMENTS

| | | | |
|---|---|---|---|
| EP | 2279707 | A1 | 2/2011 |
| EP | 2316363 | A1 | 5/2011 |
| FR | 2849590 | A1 | 7/2004 |
| WO | 2012176096 | A1 | 12/2012 |
| WO | 2013001180 | A1 | 1/2013 |

OTHER PUBLICATIONS

European Search Report dated Jun. 18, 2014 issued in European Application No. 14158813.

Australian Examination Report dated Jul. 10, 2017, issued in AU Application No. 2014201336.

Australian Office Action dated Dec. 15, 2017, issued in AU Application No. 2014201336.

International Search Report for Application No. PCT/US2017/056099 dated Jan. 8, 2018, 2 pages.

European Search Report for Application No. 17860758.6, dated May 19, 2020, 9 pages.

* cited by examiner 20
12
10
100

16
18
12
15
14

100
12
15
15
40

21
57
56
52
62
53
54
21
64a
64
67
64b
69

56
53
62a
62
58
63
62a
53

FLEXIBLE FASTENING SYSTEM

CROSS-REFERENCE TO RELATED APPLICATIONS

The present application is a continuation of U.S. patent application Ser. No. 15/614,880, filed Jun. 6, 2017, which is a continuation of U.S. patent application Ser. No. 14/203,820, now U.S. Pat. No. 9,675,386, filed Mar. 11, 2014, which claims the benefit of, and priority to, U.S. Provisional Patent Application Ser. No. 61/775,739, filed on Mar. 11, 2013. The entire contents of each of the above disclosures are incorporated herein by reference.

BACKGROUND

1. Technical Field

The present disclosure relates to implants and, more specifically, to flexible implant systems for fastening an implant to a bony element.

2. Discussion of Related Art

The spine is made up of a superposition of vertebrae, that are normally aligned along a vertebral axis, extending from the lumbar vertebrae to the cervical vertebrae, with each vertebra presenting a posterior wall from which there projects a spinous process and two side edges having walls from which there project the ribs and/or transverse processes. When an individual's spine presents abnormal curvature, the vertebrae are inclined relative to one another and relative to said vertebral axis. The lateral edges of the vertebrae situated on one side are thus closer to one another and form a concave curve, while the lateral edges on the other side appear spaced apart from one another and form a convex curve. In order to straighten the spinal column, the lateral edges of the vertebrae on the concave side are spaced apart from one another and are taken relative to one another to a distance that is substantially equivalent to the distance between the lateral edges on the other side. Thereafter, in order to keep the vertebrae in that position relative to one another, known devices are used that have screws for insertion into the vertebrae or hooks for inserting along the inside wall of the spinal canal, associated with rods for interconnecting the screws or the hooks.

The hooks are generally inserted in pairs in each vertebra and on either side close to the pedicles, the heads of the hooks projecting from the posterior wall of a vertebra, one on either side of the spinous process. The heads may be tulip-shaped to receive a rod that is secured by means of a set screw inserted in the head and bearing against the rod. Rows constituted by the heads of the hooks situated on either side of the spinous processes are interconnected and held in fixed position by two rods that are parallel to each other and to the axis of the spine.

The use of screws makes it possible to reduce the risks of such surgery. They likewise have tulip-shaped heads and are inserted in pairs in the posterior walls of vertebrae in the pedicles on either side of the spinous processes. The screws constitute fastening points in the vertebrae for holding them relative to one another. The screws are inserted into the pedicles of the vertebrae, and under certain circumstances, the pedicles may be damaged.

Wires can be used when the pedicles of the vertebrae are relatively small. However, often due to the loading on the wire and the small surface area of the wire, the wire may pull through the anatomy and thus become ineffective.

Therefore, a continuing needs exists for an implant that can address the anatomy correction, including large deformity reductions and translations needed, and still maintain the safety of the patient.

SUMMARY

Accordingly, the present disclosure relates to a flexible implant system that has a flexible implant with a surface area larger than a surgical wire to distribute the load of the implant on a bony element thereby reducing forces applied to a specific point of the anatomy and is configured to provide fastening points for spinal rods as an alternative to screws and hooks.

In an aspect of the present disclosure, a flexible implant system includes a flexible implant, an implant housing, and an implant set screw. The flexible implant is configured to loop around a portion of a bony element. The implant housing includes a housing body that defines a rod passage and an implant passage. The rod passage is configured to receive a portion of a rod and the implant passage receives a portion of the flexible implant. The implant set screw engages the flexible implant to fix the flexible implant relative to the implant housing. The implant set screw may engage the flexible implant when the flexible implant is received within the implant passage. The flexible implant system may include a rod set screw configured to engage a rod disposed within the rod passage to fix the rod relative to the implant housing. The bony element may be a vertebral body.

The flexible implant may include a leader coupled to an end of the flexible implant. The leader may be made of a malleable metal. The leader may be crimped to the flexible implant. The flexible implant may include a stiffening wire bonded to the flexible implant along a portion of the length of the flexible implant. The stiffening wire may increase the rigidity of the flexible implant. The stiffening wire may be internally bonded within the flexible implant along the entire length of the flexible implant.

In embodiments, the implant passage may include a first implant passage and a second implant passage orthogonal to the first implant passage. The flexible implant may be received within one of the first implant passage or the second implant passage. The first implant passage may be in communication with the second implant passage.

In some embodiments, the housing body defines a cutout in communication with the rod passage. The cutout may be compressed to secure a rod within the rod passage. The flexible implant system may include a rod set screw received within a first opening defined by the housing body. The first opening may be orthogonal to the cutout. The rod set screw may tighten within the first opening to compress the cutout. The housing body may have an upper body portion positioned on one side of the cutout and a lower body portion positioned on an opposite side of the cutout. The upper body portion and the lower body portion may move towards one another when the cutout is compressed.

In certain embodiments, the flexible implant system includes a tensioning instrument configured to tension the flexible implant. The tensioning instrument may include a tensioning screw and a clamping mechanism. The clamping mechanism has a clamp arm moveable between a free position and a locked position. In the free position, the flexible implant is free to slide through the clamping mechanism, and in the locked position, the flexible implant is fixed relative to the clamping mechanism. The tensioning screw may move the clamping mechanism away from the implant housing to tension the flexible implant when the clamping mechanism is in the locked position.

In aspects of the present disclosure, a method for securing a spinal rod to a bony element includes looping a flexible implant around the bony element, positioning an implant housing over the spinal rod such that the spinal rod is disposed within a rod passage of the implant housing, fixing the implant housing relative to the spinal rod, passing a portion of the flexible implant through an implant passage defined by the housing body, tensioning the flexible implant about the bony element, and securing the flexible implant relative to the implant housing. The method may include trimming an excess portion of the flexible implant after securing the flexible implant relative to the implant housing. Tensioning and securing the flexible implant may occur prior to fixing the implant housing relative to the spinal rod.

Securing the flexible implant may include inserting an implant set screw through a second opening defined by the housing body to engage the flexible implant. Looping the flexible implant around the bony element may include passing a leader of the flexible implant around the bony element and pulling the leader to draw the flexible implant around the bony element.

Tensioning the flexible implant about the bony element may include engaging the implant housing with a tensioning instrument, sliding portions of the flexible implant through a clamping mechanism of the tensioning instrument, locking the portions of the flexible implant relative to the clamping mechanism, and rotating a tensioning screw of the tensioning instrument to tension the flexible implant.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Figure 1:
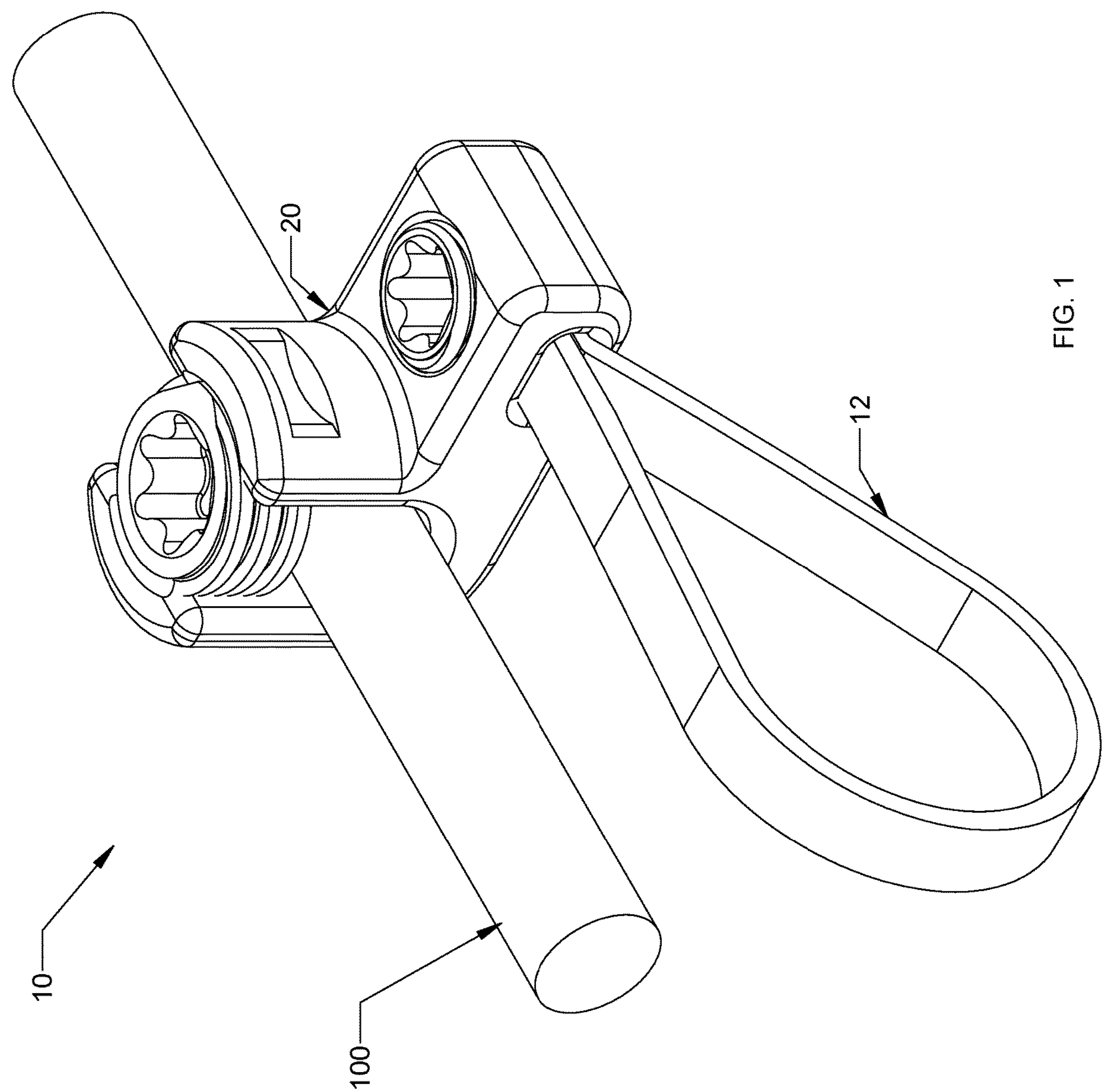
FIG. 1 is a perspective view of a spinal implant system in accordance with the present disclosure including an implant housing and a flexible implant engaged with a spinal rod.

Embodiments of the present disclosure are now described in detail with reference to the drawings in which like reference numerals designate identical or corresponding elements in each of the several views. As used herein, the term “clinician” refers to a doctor, a nurse, or any other care provider and may include support personnel. Throughout this description, the term “proximal” will refer to the portion of the device or component thereof that is closest to the clinician and the term “distal” will refer to the portion of the device or component thereof that is farthest from the clinician. In addition, the term “cephalad” is used in this application to indicate a direction toward a patient’s head, whereas the term “caudad” indicates a direction toward the patient’s feet. Further still, for the purposes of this application, the term “lateral” indicates a direction toward a side of the body of the patient, i.e., away from the middle of the body of the patient. The term “posterior” indicates a direction toward the patient’s back, and the term “anterior” indicates a direction toward the patient’s front. Additionally, in the drawings and in the description that follows, terms such as front, rear, upper, lower, top, bottom, and similar directional terms are used simply for convenience of description and are not intended to limit the disclosure.

Referring now to FIG. 1 a flexible implant system 10 is provided in accordance with the present disclosure and includes a flexible implant 12 and an implant housing 20. The flexible implant 12 forms a loop around a bony element (see FIG. 7B) of a patient's anatomy and is secured to the bony element by the implant housing 20 as detailed below. Although shown and described in the context of spinal surgery, it is contemplated that the presently disclosed flexible implant system 10 may be coupled to other bony elements in a patient. The implant housing 20 provides a mounting point for a rod 100. It is within the scope of this disclosure that a plurality of flexible implant systems 10 may be used to provide a plurality of mounting points along a bony element of a patient's anatomy. It is also contemplated that the flexible implant system 10 may be used with spinal hooks (not shown) and pedicle screws (not shown) to provide a plurality of mounting points along a bony element of a patient's anatomy.

Figure 2:
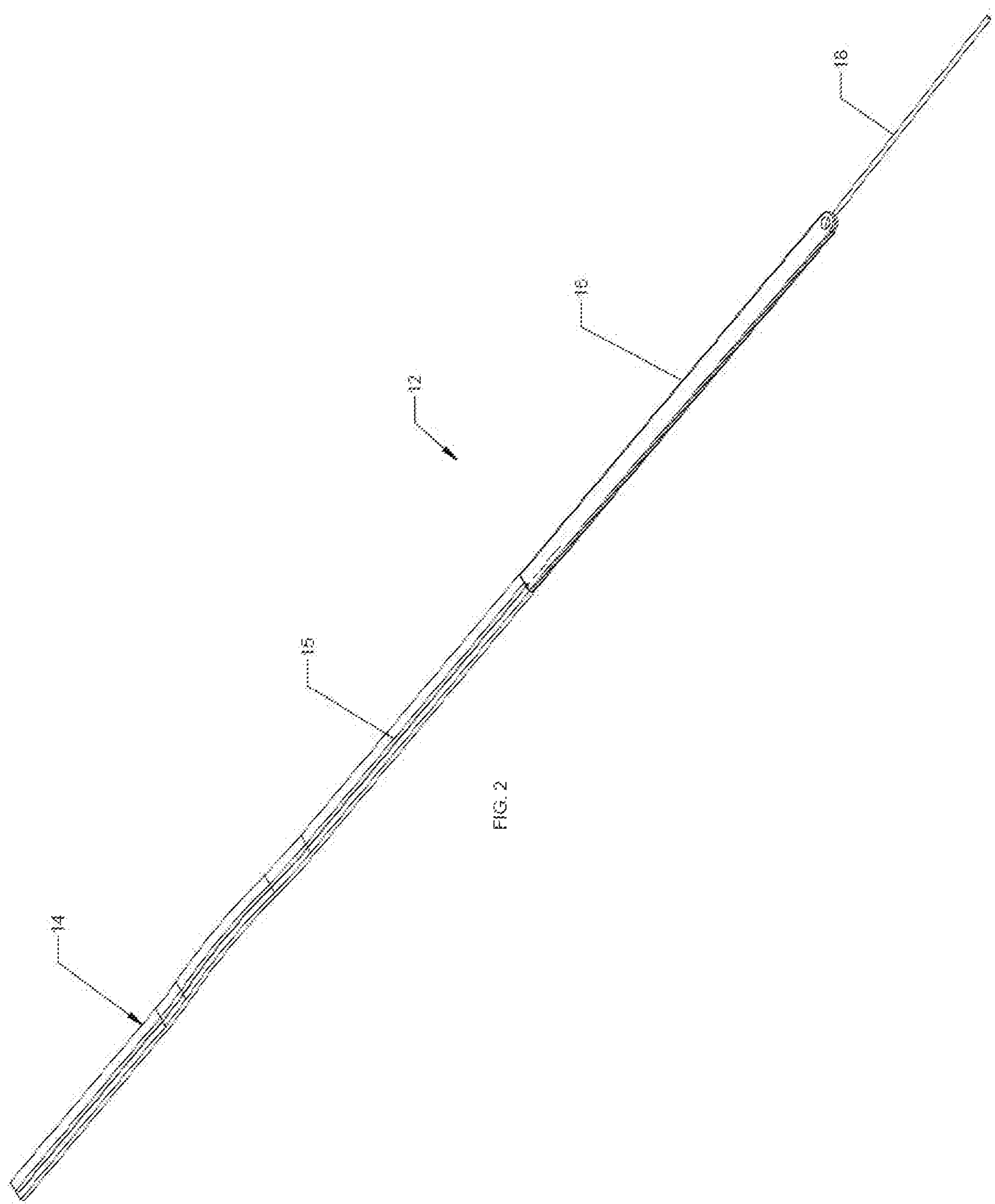
FIG. 2 is a perspective view of the flexible implant of FIG. 1.
Figure 3:
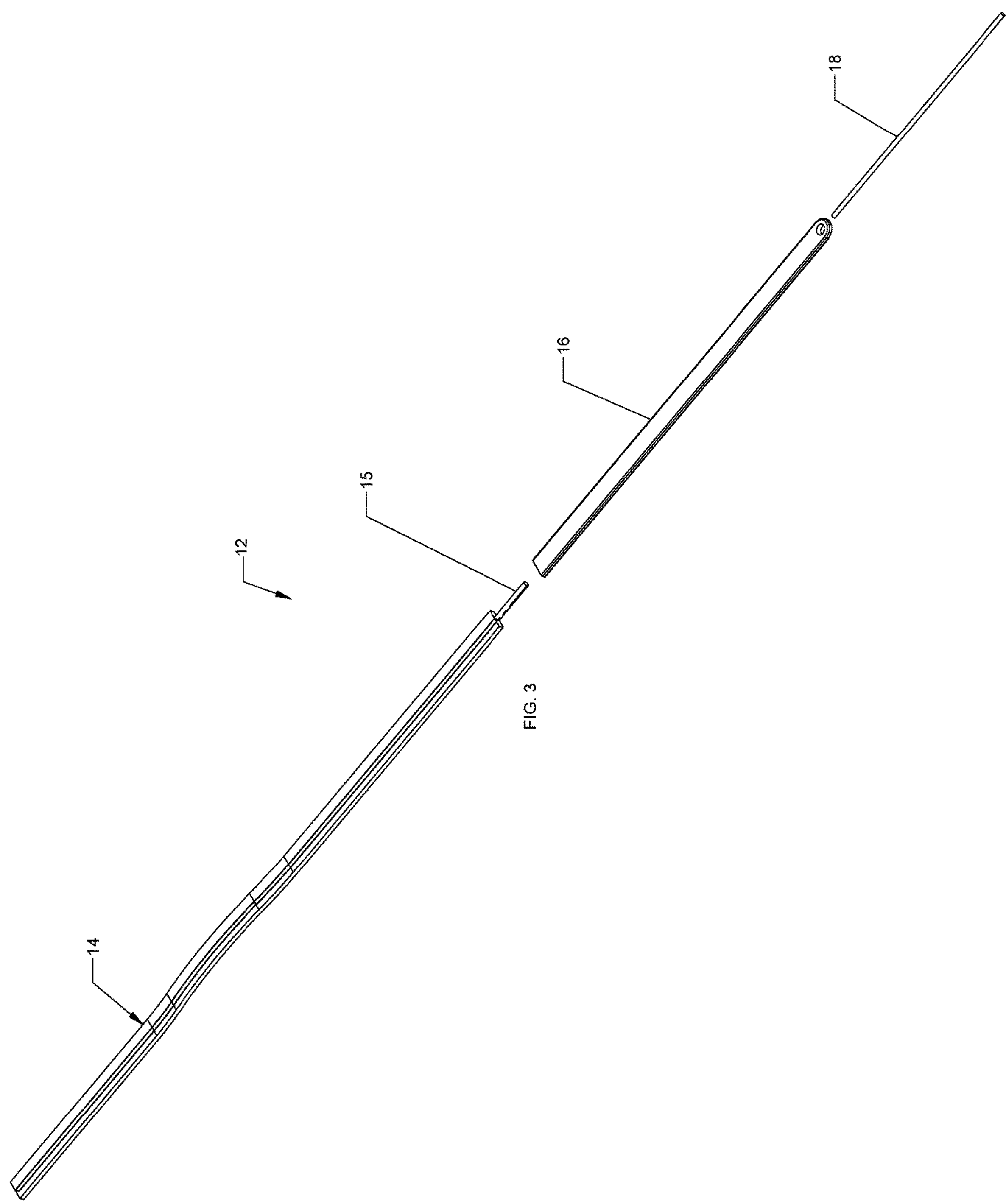
FIG. 3 is an exploded view showing the components of the flexible implant of FIG. 2.

With reference to FIGS. 2 and 3, the flexible implant 12 includes an implant body 14, a leader 16, and a guide wire 18. The implant body 14 may be made from various polymers including but not limited to nylon, Dacron®, Ultra-High-Molecular-Weight Polyethylene (UHMWPE), polypropylene, polyester, etc. The implant body 14 may include a stiffening wire to increase the stiffness of the implant body 14. The stiffening wire 15 may be internally bonded (i.e., bonded within the implant body 14) or may be externally bonded (i.e., bonded on an external surface of the implant body 14). The stiffening wire 15 may be bonded along the entire length of the implant body 14 or only a portion of the length of the implant body 14.

The leader 16 may be made of a malleable metal that is attached to an end of the implant body 14. The leader 16 may be attached to implant body 14 by various techniques including but not limited to crimping, ultrasonic welding, sewing, gluing, etc. The leader 16 may assist in inserting the flexible implant 12 through or around the anatomy of a patient or tensioning the flexible implant 12 as detailed below. The leader may be made from a radiopaque plastic material.

The guide wire 18 is attached to an end of the leader 16 opposite of the end attached to the end of the implant body 14. In embodiments, the guide wire 18 may be made of polyester or other like material. In some embodiments, the guide wire 18 is made of malleable metal bonded or crimped to the leader 16. The guide wire 18 is bonded or crimped to the leader 16. The guide wire 18 is flexible to assist in inserting and guiding the flexible implant 12 through or around the anatomy of a patient as detailed below. It is also within the scope of this disclosure that the guide wire 18 is attached directly to the end of the implant body 14 and extends through the leader 16. Moreover, it is contemplated that the flexible implant 12 does not include a leader 16 and that the guide wire 18 is attached directly to the end of the implant body 14 or that the guide wire 18 is an end of the stiffening wire 15 extending from the end of the implant body 14.

Figure 4:
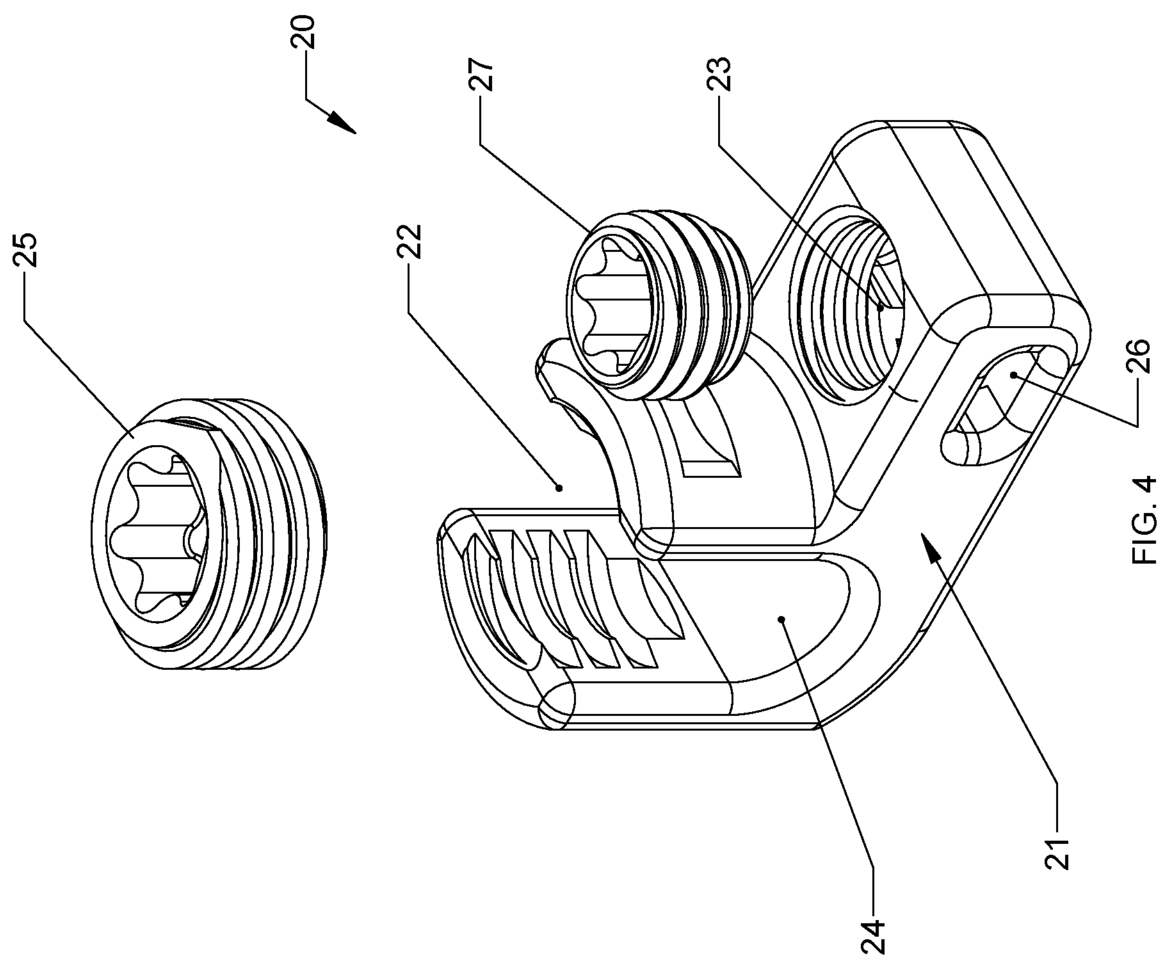
FIG. 4 is a perspective view of the implant housing of FIG. 1 with the set screws removed from their respective openings.
Figure 5:
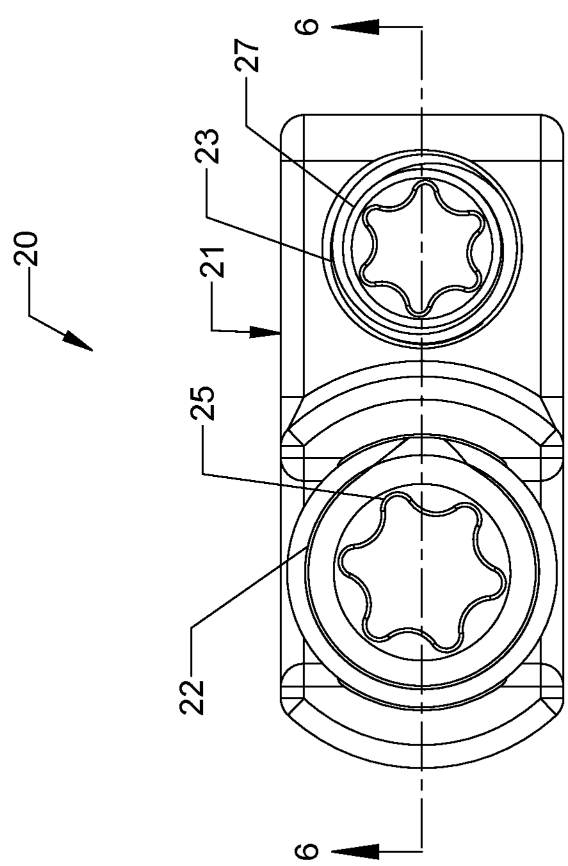
FIG. 5 is a top view of the implant housing of FIG. 1.
Figure 6:
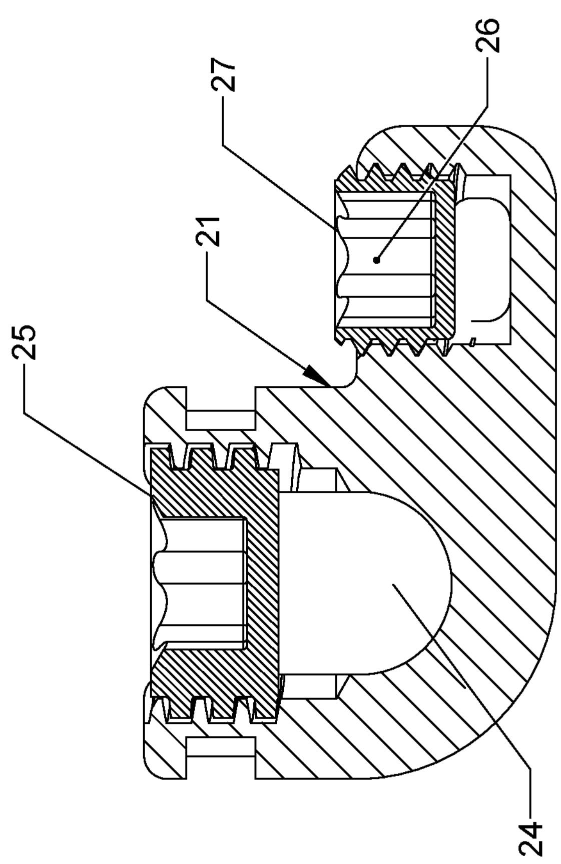
FIG. 6 is a side cross-sectional view taken along section line 6-6 of FIG. 5.

Referring to FIGS. 4-6, the implant housing 20 includes a housing body 21, a rod set screw 25, and an implant set screw 27. The housing body 21 defines a first opening 22, a second opening 23, a rod passage 24, and an implant passage 26. The rod passage 24 is sized and configured to receive a portion of a rod (e.g., spinal rod 100) therein. The rod passage 24 is in communication with the first opening 22. The rod passage 24 may be a U-shaped channel through an upper surface of the housing body 21. The upper portion of the rod passage 24 may form the first opening 22. It will be appreciated that implant housing 20 may be positioned about a rod in situ. The rod set screw 25 is insertable through the first opening 22 such that that rod set screw 25 secures the rod within the rod passage 24 as detailed below. The implant passage 26 is sized and configured to slidably receive the flexible implant 12 and is in communication with the second opening 23. The implant set screw 27 is insertable through the second opening 23 such that the implant set screw 27 secures the flexible implant 12 within the implant passage 26. The set screws 25, 27 may directly engage the rod and the flexible implant 12, respectively, to fix the rod and the flexible implant 12 relative to the implant housing 20. It will be appreciated that the set screws 25, 27 may include threads that cooperate with features (e.g., threads) of the first and second openings 22, 23, respectively, to secure the rod and the flexible implant 12 within the rod passage 24 and the implant passage 26, respectively.

Figure 7A:
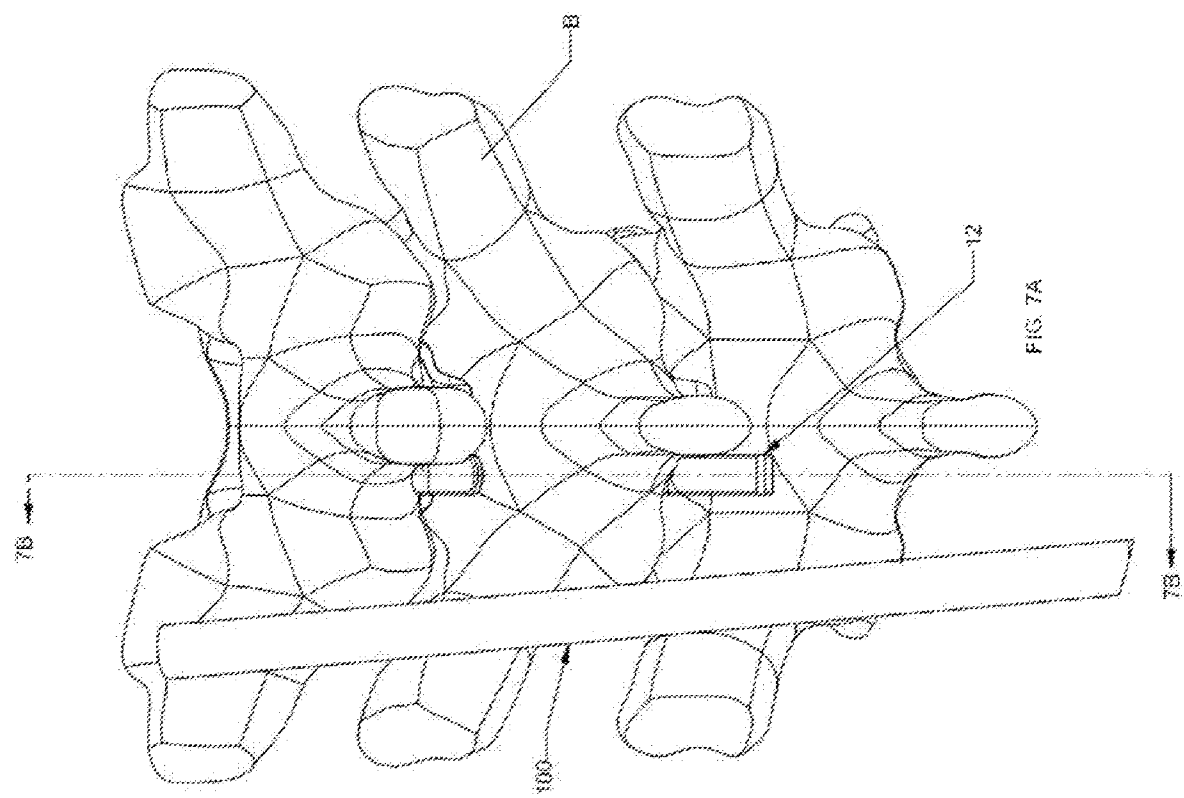
FIG. 7A is a posterior view of a spinal process of a patient with a spinal rod positioned along the spinal process and the flexible implant of FIG. 2 being threaded around a vertebral body.
Figure 7B:
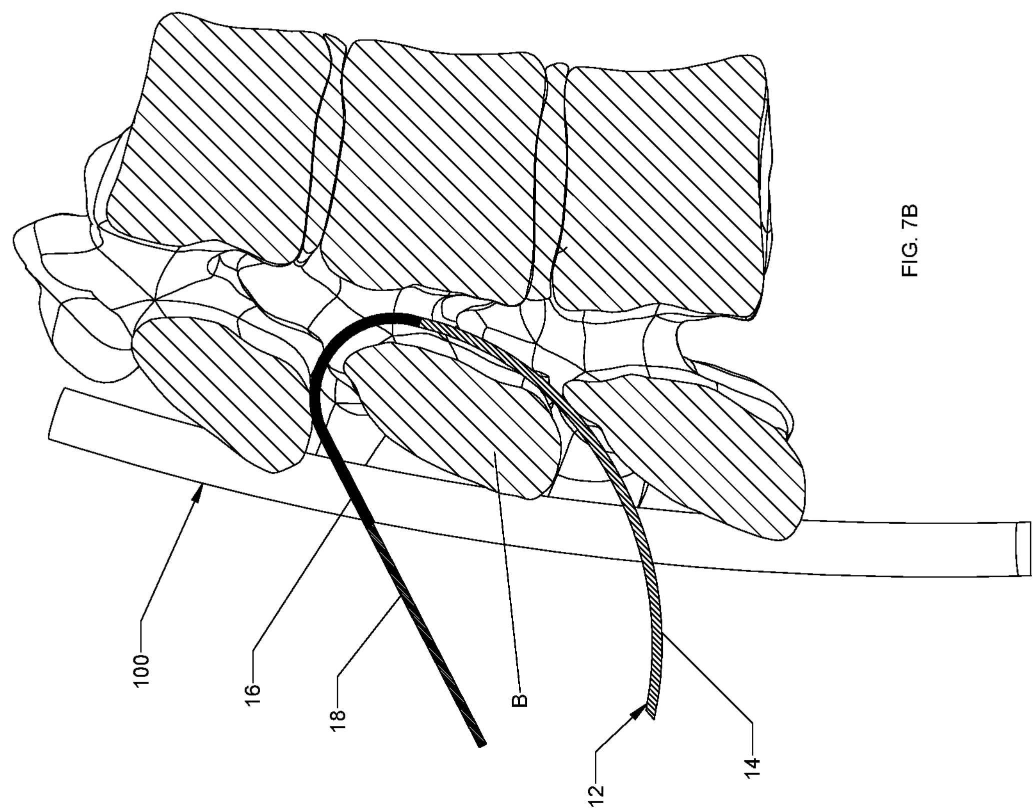
FIG. 7B is a lateral cross-sectional view taken along section line 7B-7B of FIG. 7A.
Figure 8A:
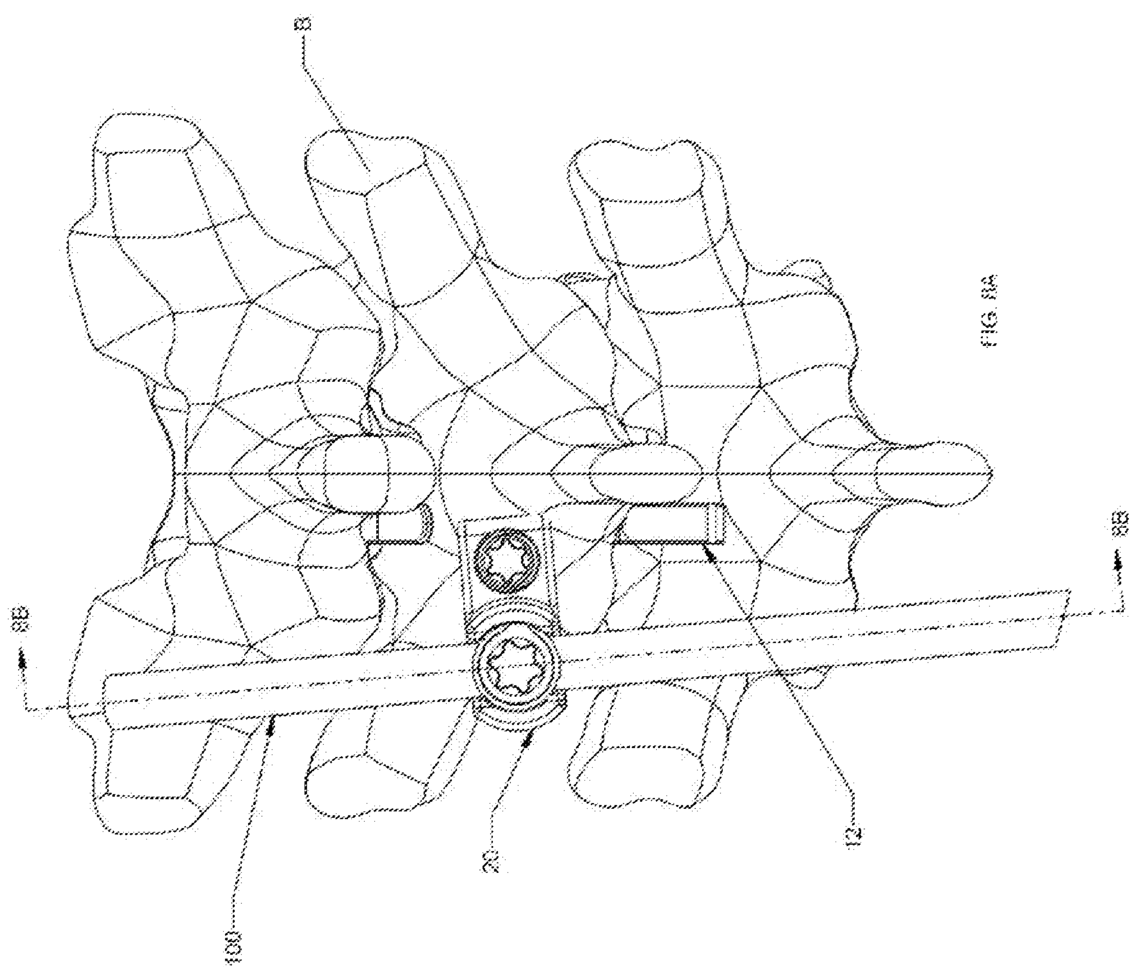
FIG. 8A is a posterior view of the spinal process of FIG. 7A with the implant housing of FIG. 4 engaged with the spinal rod.
Figure 8B:
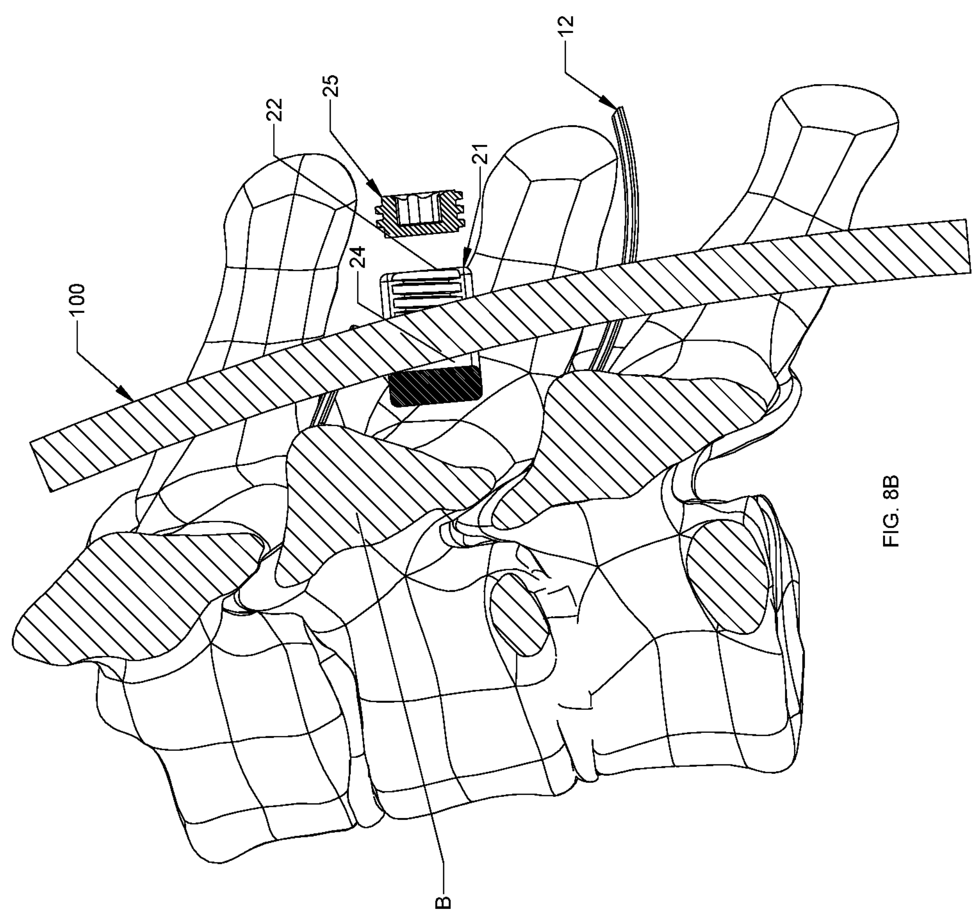
FIG. 8B is a lateral cross-sectional view taken along section line 8B-8B of FIG. 8A.
Figure 9A:
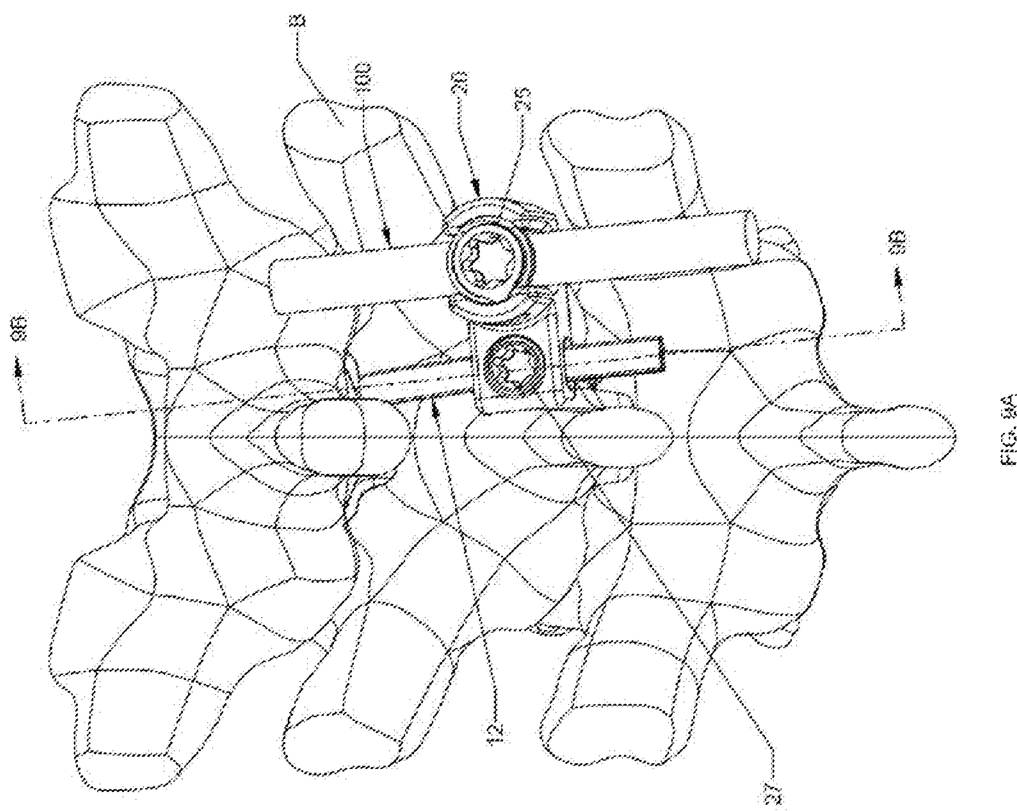
FIG. 9A is a posterior view of a spinal process of FIG. 8A with ends of the flexible implant 12 passed through an implant passage in the implant housing.
Figure 9B:
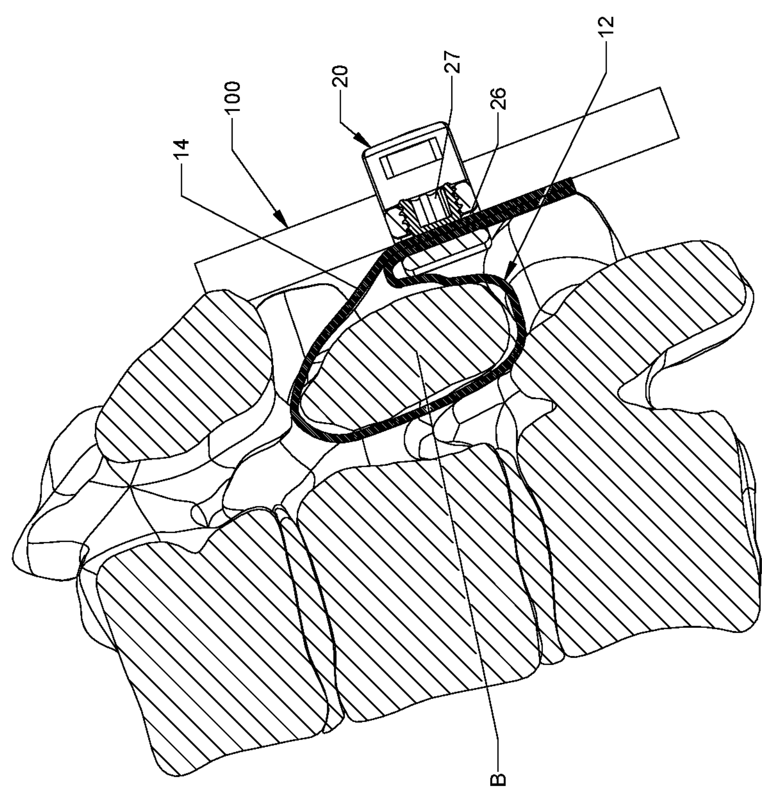
FIG. 9B is a lateral cross-sectional view taken along section line 9B-9B of FIG. 9A.
Figure 10:
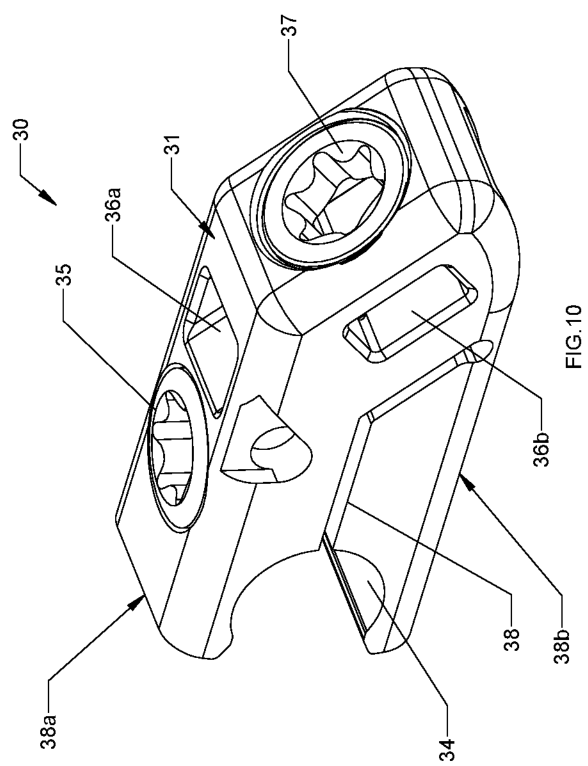
FIG. 10 is a perspective view of another implant housing in accordance with the present disclosure including a compressible cutout.
Figure 11:
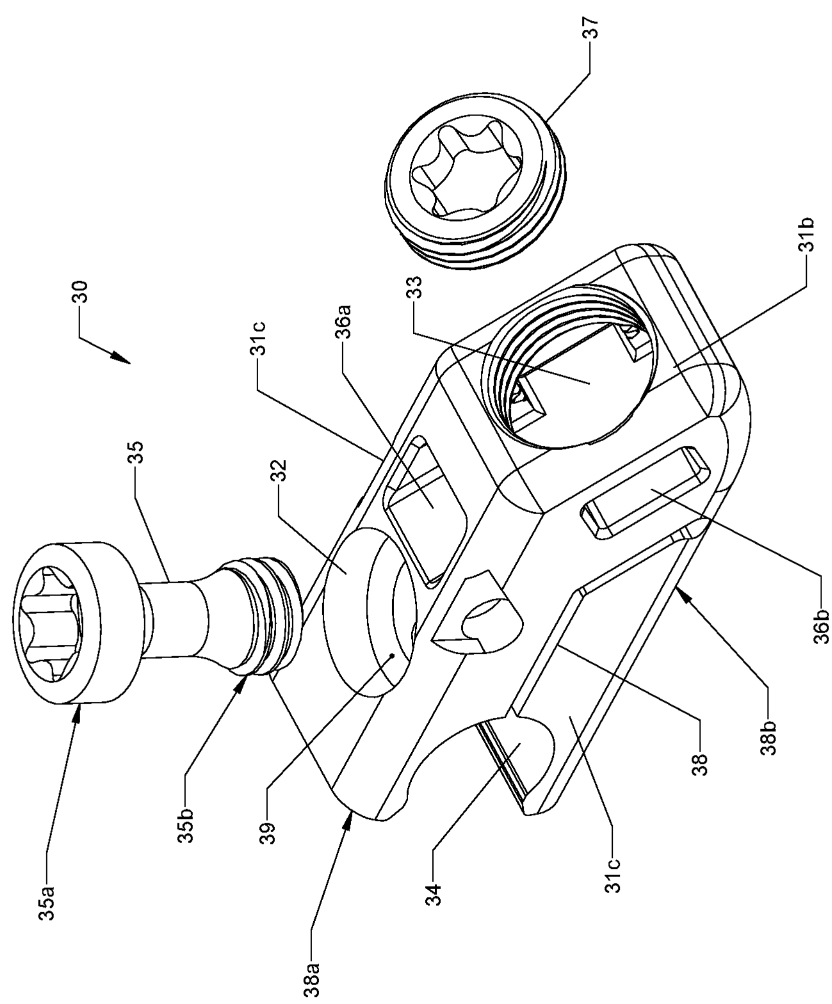
FIG. 11 is a perspective view of the implant housing of FIG. 10 with the set screws removed from their respective openings.

Referring to FIGS. 7A-9B, the spinal implant system 10 is positioned about a vertebral body B of a patient to provide a fastening point for a spinal rod 100. The guide wire 18 of the flexible implant 12 is used to guide the leader 16 and implant body 14 of the flexible implant 12 around a portion of the vertebral body B as shown in FIGS. 7A and 7B. The implant housing 20 is positioned about the spinal rod 100 adjacent the flexible implant 12 with the spinal rod 100 received within the rod passage 24. The implant housing 20 may be adjusted to a desired position relative to the spinal rod 100 and the vertebral body B. The rod set screw 25 is inserted into the first opening 22 of the implant housing 20 and tightened to fix the implant housing 20 relative to the spinal rod 100 in the desired position as shown in FIGS. 8A and 8B. Each end of the flexible implant 12 is inserted through the implant passage 26 of the implant housing 20. The flexible implant 12 is positioned within the implant passage 26 such that the implant body 14 is positioned around the vertebral body B and received through the implant passage 26 of the implant housing 20. When the flexible implant 12 is received through the implant passage 26, the ends of the flexible implant 12 are pulled to tension the flexible implant 12 about the vertebral body B as detailed below.

When the flexible implant 12 is tensioned about the vertebral body B, the implant set screw 27 is inserted into the second opening 23 and tightened to fully fix the flexible implant 12 to the implant housing 20. It is also within the scope of this disclosure that the implant set screw 27 may be inserted into the second opening 23 and tightened to partially fix the flexible implant 12 to the implant housing 20 before the flexible implant 12 is tensioned. After the flexible implant 12 is fully fixed to the implant housing 20, any excess portion of the flexible implant 12 passing through the implant housing 20 may be trimmed with a scissors, shears, or other suitable instrument.

It is also within the scope of this disclosure that the flexible implant 12 may be positioned and/or tensioned about the vertebral body B before the implant housing 20 is coupled to the rod 100.

With reference to FIGS. 10-13, another implant housing 30 is provided in accordance with the present disclosure and includes a housing body 31, a rod set screw 35, and an implant set screw 37. The housing body 31 defines a first opening 32, a second opening 33, a rod passage 34, a first implant passage 36*a*, a second implant passage 36*b*, and a compressible cutout 38. The rod passage 34 is sized and configured to receive a portion of a rod (e.g., spinal rod 100) therein. The rod passage 34 may be a U-shaped channel through a rear surface 31*a* of the housing body 31. The compressible cutout 38 passes through side surfaces 31*c* of the housing body 31 substantially orthogonal to the side surfaces 31*c*. The compressible cutout 38 is between an upper body portion 38*a* and a lower body portion 38*b* of the housing body 31. The first opening 32 passes through the upper and lower surfaces of the housing body 31 substantially parallel to the rear surface 31*a* of the housing body 31 and passes through the compressible cutout 38. A first portion 32*a* of the first opening 32 is adjacent the upper surface of the housing body 31 and defines a first diameter $D_1$ through the upper body portion 38*a*. A second portion 32*b* of the first opening 32 extends from the first portion 32*a*, through the compressible cutout 38, and through the lower surface of the housing body 31 and defines a second diameter $D_2$ through the lower body portion 38*b*. The first diameter $D_1$ is smaller than the first diameter $D_1$. A landing 39 may be defined between the first and the second portions 32*a*, 32*b*. The second portion 32*b* may include a threaded portion 32*c* in the lower body portion 38*b*. The rod set screw 35 is insertable through the first opening 32 such that a head 35*a* of the rod set screw 35 engages the landing 39 as a threaded portion 35*b* of the rod set screw 35 cooperates with the threaded portion 32*c* of the first opening 32. As the head 35*a* engages the landing 39 the compressible cutout 38 is compressed to reduce a diameter of the rod passage 34 to fix the implant housing 30 to the rod received within the rod passage 34. The upper and lower body portions 38*a*, 38*b* are moved towards one another as the compressible cutout 38 is compressed. This frictional engagement between the rod 100 and the implant housing 30 secures the axial position of the rod 100 with respect to the implant housing 30. It will be appreciated that this frictional engagement also applies to the housing 20 detailed above.

Figure 12:
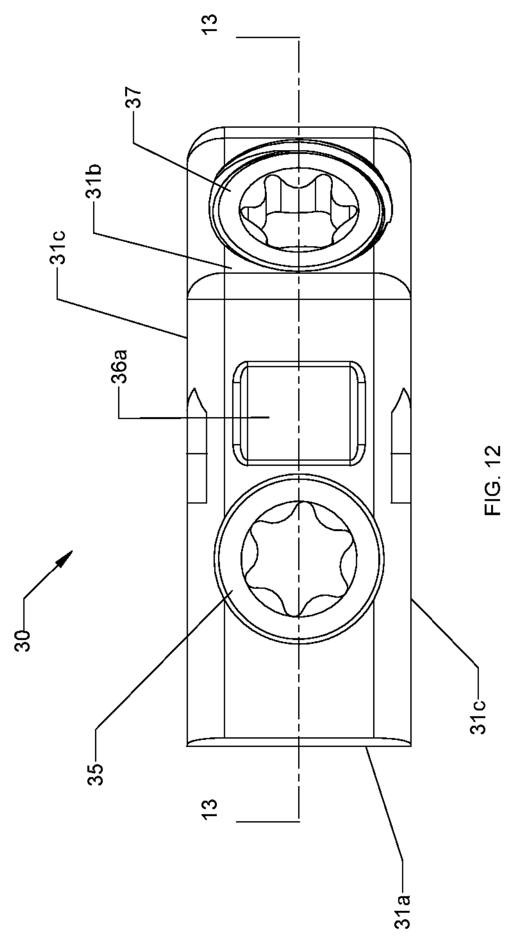
FIG. 12 is a top view of the implant housing of FIG. 10.
Figure 13:
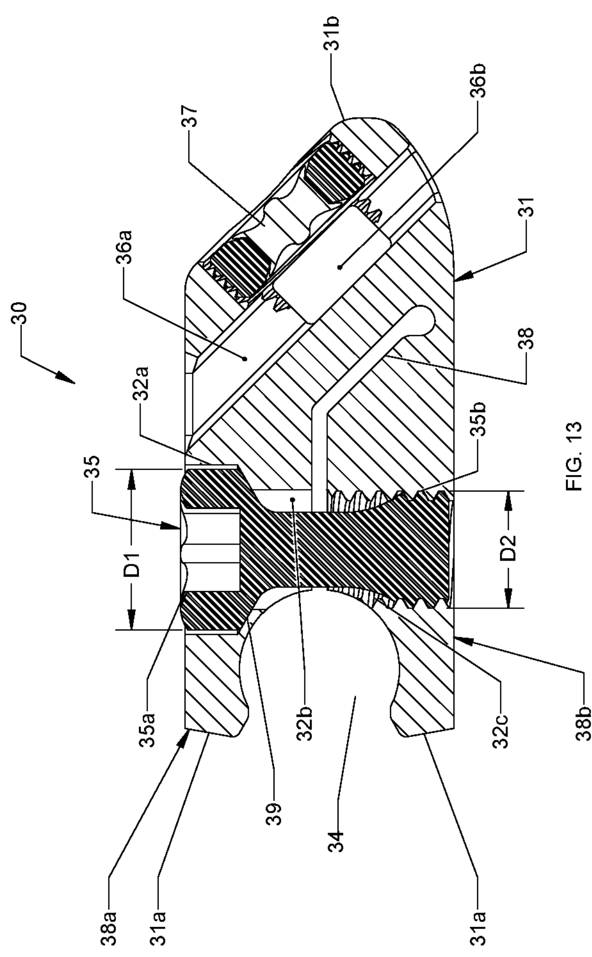
FIG. 13 is a cross-sectional view taken along the section line 13-13 of FIG. 12.
Figure 14:
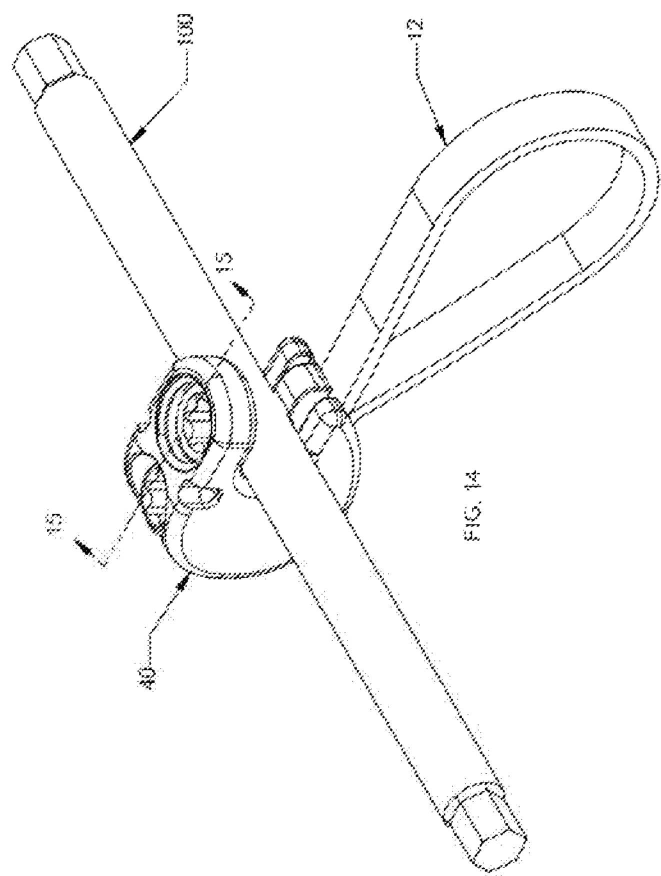
FIG. 14 is a perspective view of yet another implant housing in accordance with the present disclosure engaged with a spinal rod and the flexible implant of FIG. 2.
Figure 15:
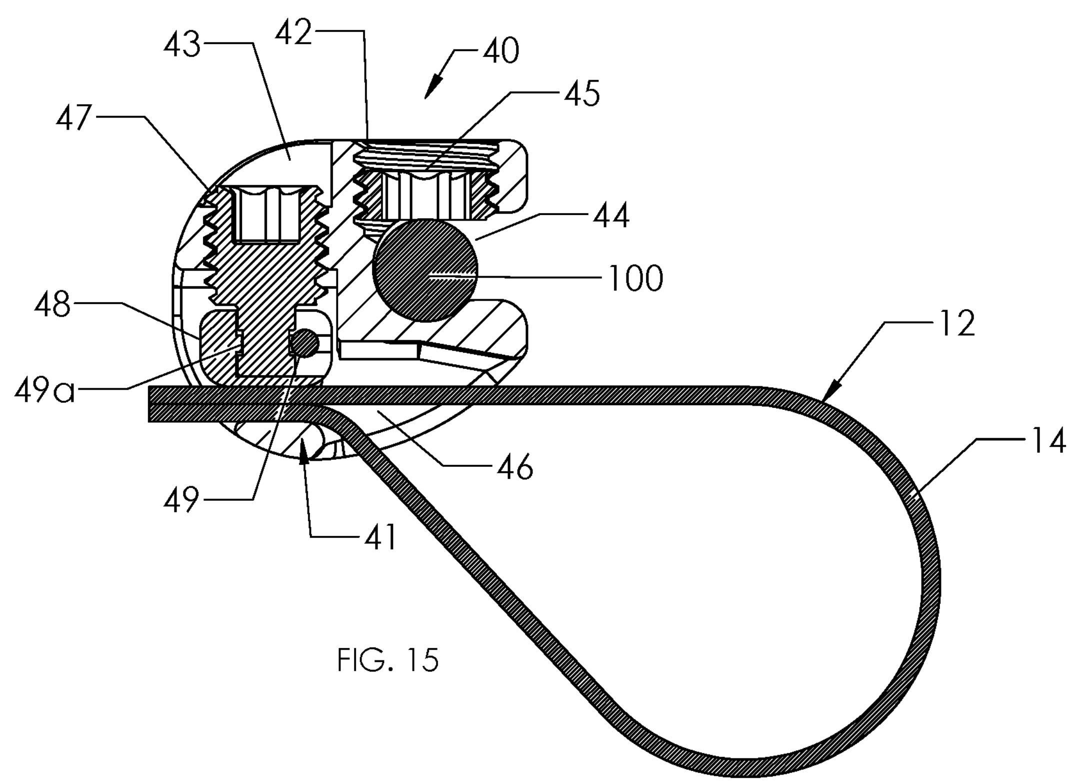
FIG. 15 is a cross-sectional view taken along section line 15-15 of FIG. 14.
Figure 16:
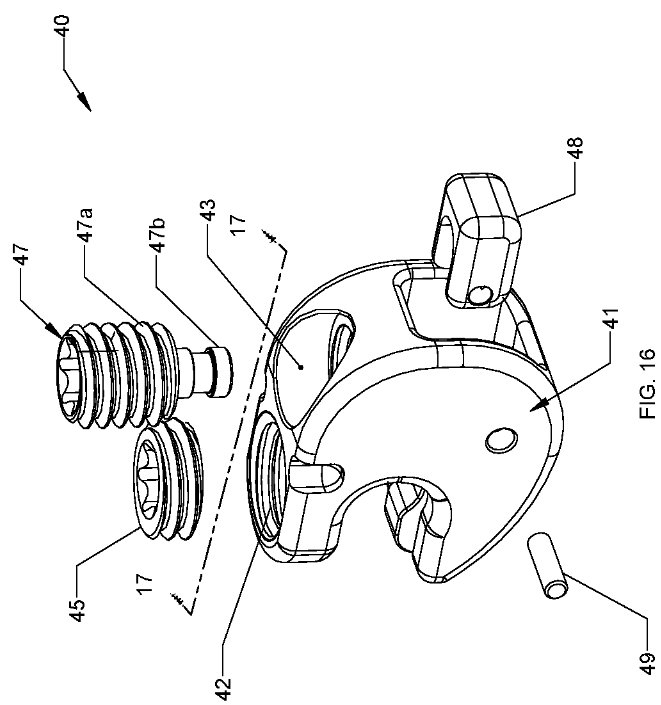
FIG. 16 is a rear perspective view of the implant housing of FIG. 14 with the set screws removed from their respective openings and a chock removed from the implant housing.

The first implant passage 36*a* passes through the upper and lower surfaces of the housing body 31 and the second implant passage 36*b* is substantially orthogonal to the first implant passage 36*a* passing through the side surfaces 31*c* of the housing body 31. The first and second implant passages 36*a*, 36*b* are each in communication with the second opening 33. The first and second implant passages 36*a*, 36*b* may be in communication with one another. The second opening 33 is defined in a front surface 31*b* of the housing body 31. As shown in FIGS. 12 and 13, the front surface 31*b* may be oblique to the rear surface 31*a*; however, it is also contemplated that the front surface 31*b* may be parallel to the rear surface 31*a*. The first and second implant passages 36*a*, 36*b* and the second opening 33 function substantially similar to the implant passage 36 and the second opening 33 detailed above while providing greater flexibility to the positioning of the implant housing 30 relative to a flexible implant (e.g., flexible implant 12) and a rod (e.g., spinal rod 100).

Figure 17:
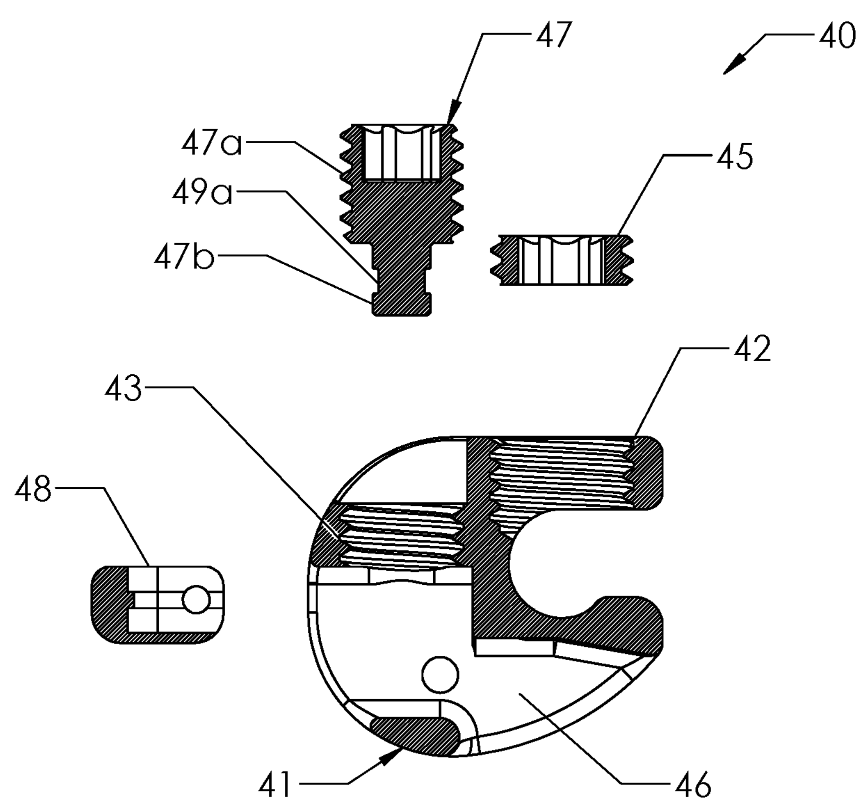
FIG. 17 is a cross-sectional view taken along section line 17-17 of FIG. 16.
Figure 18:
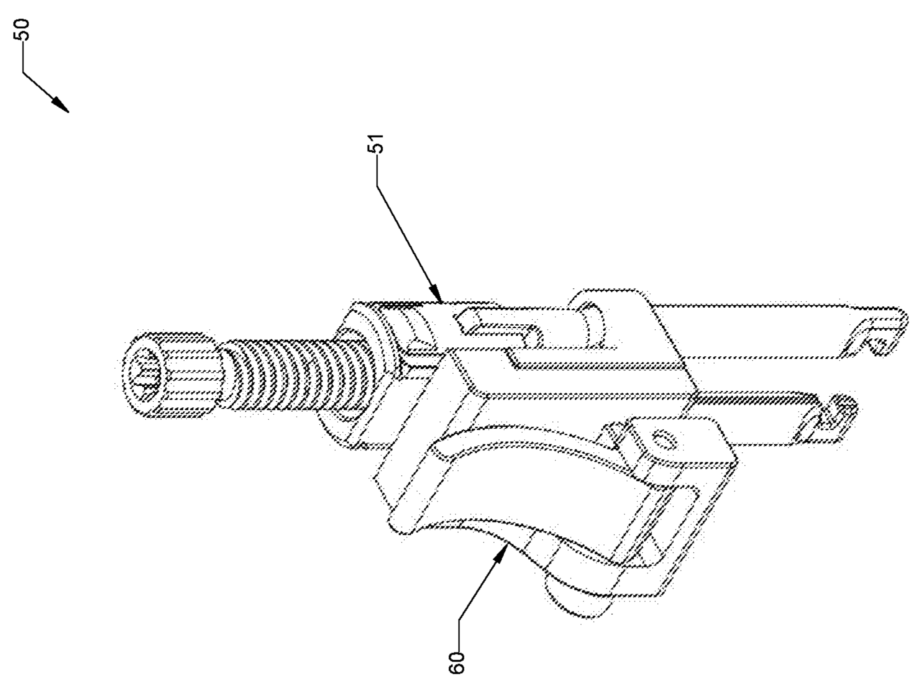
FIG. 18 is a perspective view of a tensioning instrument in accordance with the present disclosure.
Figure 19:
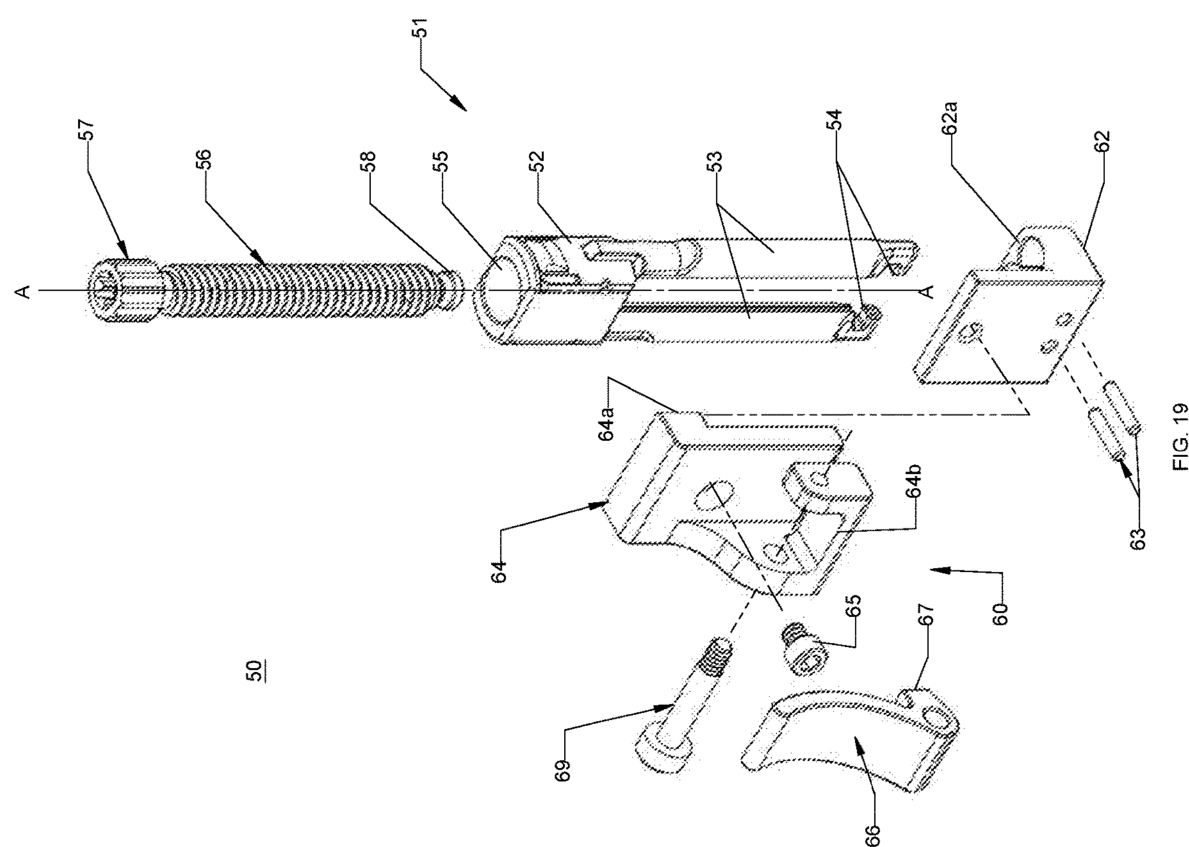
FIG. 19 is an exploded view showing the components of the tensioning instrument of FIG. 18.
Figure 20:
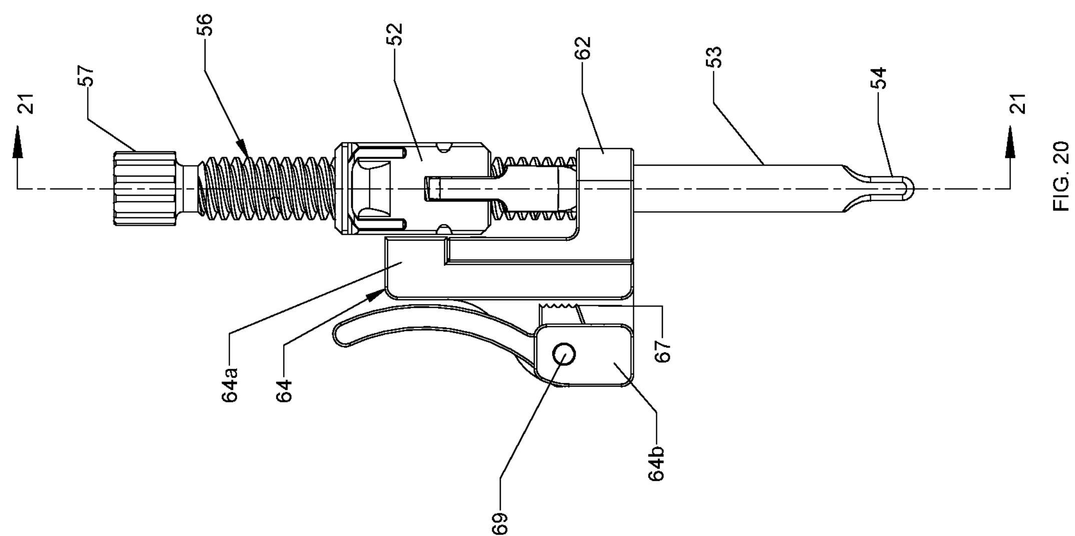
FIG. 20 is a side view of the tensioning instrument of FIG. 18.

With reference to FIGS. 14-17, yet another implant housing 40 provided in accordance with the present disclosure includes a housing body 41, a rod set screw 45, an implant set screw 47, and an implant chock 48. The housing body 41 defines a first opening 42, a second opening 43, a rod passage 44, and an implant passage 46. The rod passage 44 is sized and configured to receive a portion of a rod (e.g., spinal rod 100) therein. The rod passage 44 is in communication with the first opening 42. The rod passage 44 may be a U-shaped channel through a surface of the housing body 41. In some embodiments, the first opening 42 is parallel to the surface of the housing body 41 through which the rod passage 44 passes as shown in FIG. 17. In other embodiments, a portion of the rod passage 45 may form the first opening 42. The rod set screw 45 is insertable through the first opening 42 such that that rod set screw 45 secures the rod within the rod passage 44. The rod may be axially and rotationally secured within the rod passage 44.

The implant passage 46 is sized and configured to slidably receive the flexible implant 12 and is in communication with the second opening 43. The implant passage 46 may be substantially orthogonal to the second opening 43 as shown in FIG. 17. The implant chock 48 is positioned within the implant passage 46 and aligned with the second opening 43. The implant chock 48 is retained within the implant passage 46 by a chock pin 49 passing through side surfaces of the housing body 41 and the implant chock 48. The implant chock 48 may rotate about the chock pin 49. The implant set screw 47 is insertable through the second opening 43 such that the implant set screw 47 engages the implant chock 48. In some embodiments, a portion of the implant set screw 47 engages the chock pin 49 such that the implant set screw 47 is retained within the second opening 43 by the cooperation of the chock 48 and the chock pin 49. For example, the implant set screw 47 may include a threaded portion 47*a* and an engagement portion 47*b* extending from the threaded portion 47*a*. The engagement portion 47*b* defining recesses 49*a* to rotatably receive a portion of the chock 48 or the chock pin 49. As the implant set screw 47 is rotated, the engagement portion 47*b* engages the chock 48 to fix the flexible implant 12 between the chock 48 and a portion of the implant housing 41. As the engagement portion 47*b* engages the chock 48, the chock 48 may rotate such that a lead portion 48*a* of the chock 48 is wedged into the flexible implant 12 to prevent the flexible implant 12 from sliding within the implant passage 46. In some embodiments, the rotation of the chock 48 may permit the flexible implant 12 to slide in one direction within the implant passage 46 to apply tension to a portion of the flexible implant 12 positioned about a bony element (e.g., in the direction of arrow T in FIG. 15) and prevent the flexible implant 12 from sliding in a second direction opposite the first direction within the implant passage 46 (e.g., in the direction opposite that of the arrow T in FIG. 15).

Referring now to FIGS. 18-22, a tensioning instrument 50 may be used in accordance with the present disclosure to tension the flexible implant 12 (FIG. 1) within an implant housing (e.g., implant housings 20, 30, or 40). The tensioning instrument 50 includes a tensioning mechanism 51 and a clamping mechanism 60. The tensioning mechanism 51 includes a tensioning body 52 defining a longitudinal axis A-A. The tensioning body 52 includes arms 53 extending parallel to the longitudinal axis A-A. The arms 53 terminate in fingers 54 that are configured to engage a portion of the housing as detailed below. The arms 53 may be pivotable away from the longitudinal axis A-A to engage the housing and lockable when engaged with the housing. The tensioning body 52 further defines a threaded hole 55 along the longitudinal axis A-A. The threaded hole 55 receives a tensioning screw 56. The tensioning screw 56 includes a head 57 adjacent a proximal end thereof and a tensioning disc 58 adjacent a distal end thereof.

Figure 21:
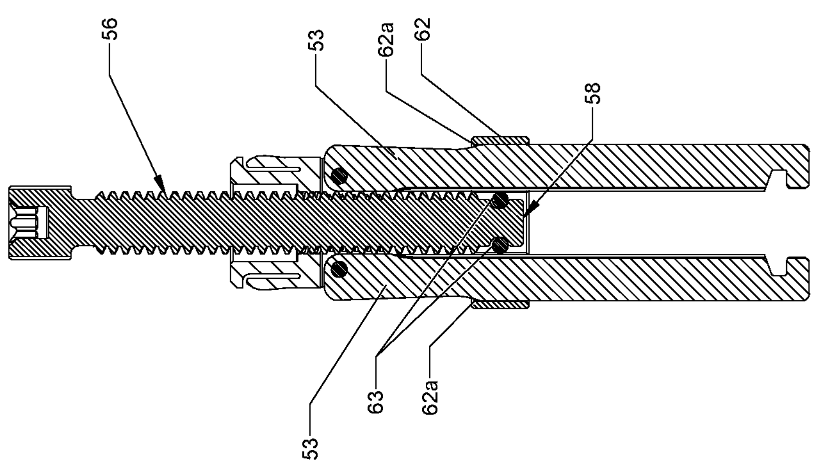
FIG. 21 is a cross-sectional view taken along section line 21-21 of FIG. 20.
Figure 22:
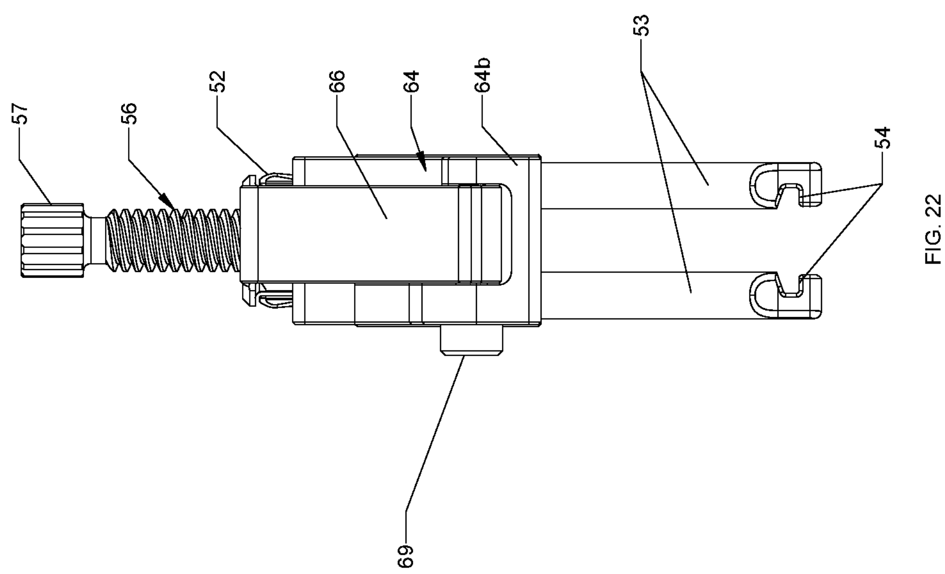
FIG. 22 is a front view of the tensioning instrument of FIG. 18.

The clamping mechanism 60 includes a receiver 62, a clamp base 64, and a clamp arm 66. The receiver 62 defines openings 62*a* sized to permit the arms 53 to pass through the receiver 62. A pair of disc pins 63 are received within the receiver 62 about the tensioning screw 56 proximal to the tensioning disc 58 such that the tensioning screw 56 is retained within the threaded hole 55 and fixed relative to the receiver 62 as shown in FIG. 21. The clamp base 64 is coupled to the receiver 62 by a base screw 65. The clamp base 64 may include a protrusion 64*a* align the clamp base with the receiver 62. The clamp base 64 includes an arm mount 64*b* configured to pivotally retain the clamp arm 66. A pivot screw 69 passes through the arm mount 64*b* and the clamp arm 66 to retain the clamp arm 66 to the clamp base 64. The clamp arm 66 includes an implant engagement portion 67 to capture the flexible implant 12 between the clamp arm 66 and the clamp base 64 as detailed below. The implant engagement portion 67 may include teeth.

Figure 23:
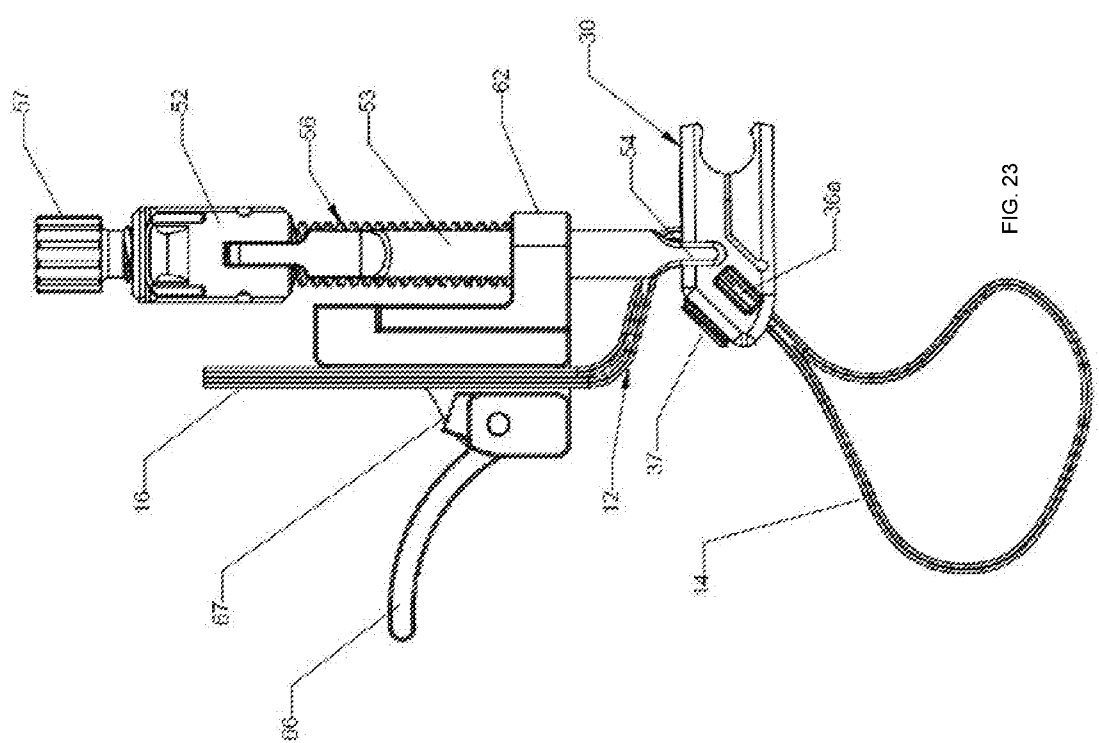
FIG. 23 is a side view of the tensioning instrument of FIG. 18 engaged with the implant housing of FIG. 10 and the flexible implant of FIG. 2 illustrating a clamp arm of the tensioning instrument in a free position.
Figure 24:
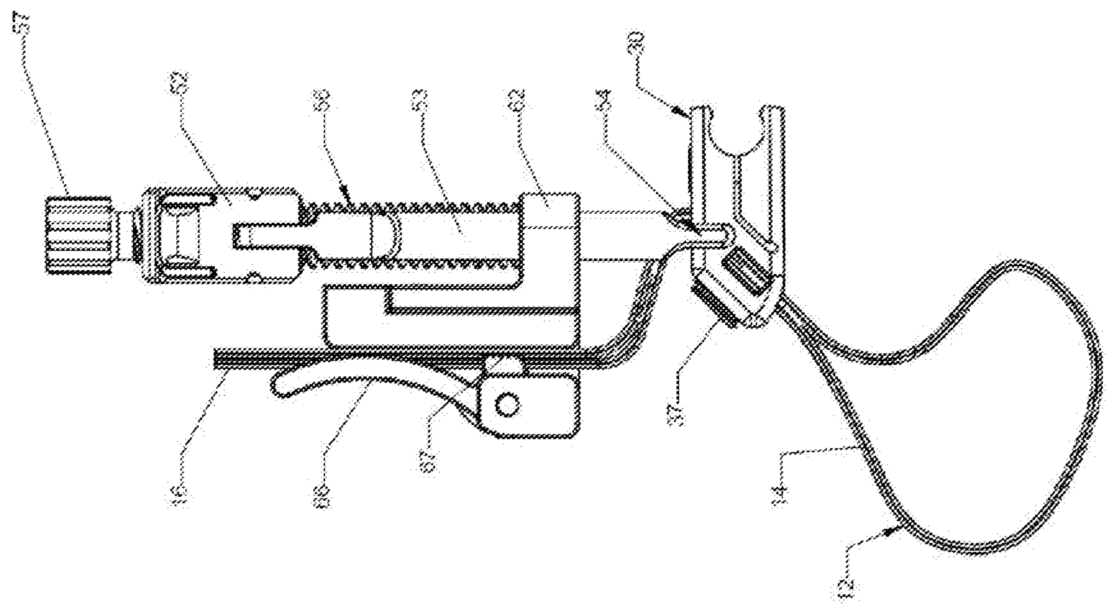
FIG. 24 is a side view of the tensioning instrument of FIG. 23 with the clamp arm in a locked position and a head of a tensioning screw adjacent a tensioning body.
Figure 25:
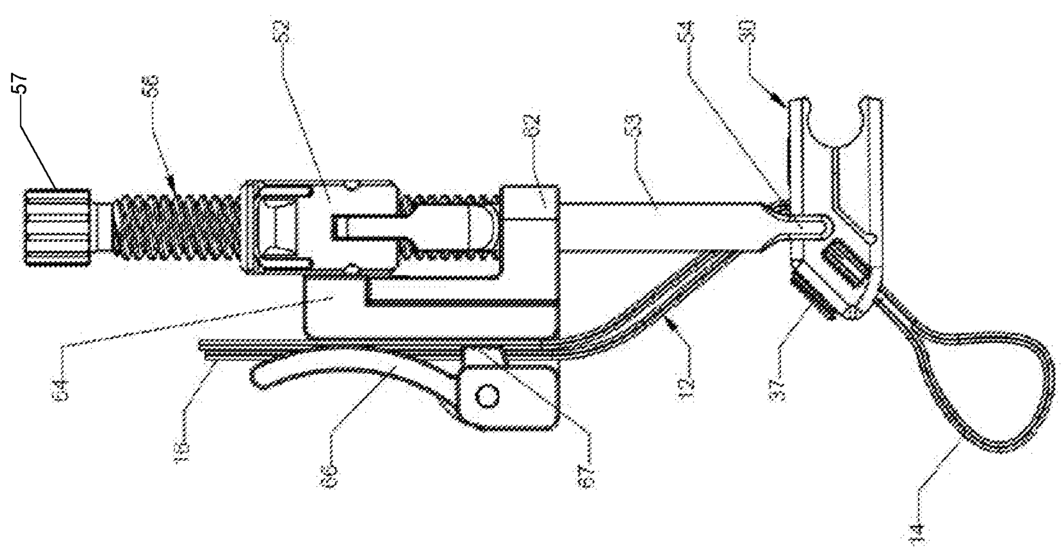
FIG. 25 is a side view of the tensioning instrument of FIG. 24 with the clamp arm in the locked position and the flexible implant tensioned.

With reference to FIGS. 23-25, when the flexible implant 12 is looped around a vertebral body B (FIG. 9B) as detailed above, the tensioning instrument 50 may be used to tension the flexible implant 12 before the implant set screw (e.g., implant set screw 27, 37, 47) is tightened to fix the flexible implant 12. As shown, the tensioning instrument 50 is used with the implant housing 30; however, it should be appreciated that the tensioning instrument 50 may be used with any of the implant housings disclosed herein (e.g., implant housings 30, 30, or 40).

With particular reference to FIG. 23, the fingers 54 of the arms 53 engage the implant housing 30 to longitudinally fix the tensioning body 52 relative to the implant housing 30. The ends of the flexible implant 12 are passed through the first implant passage 36*a* of the implant housing 30 and then passed between the clamp arm 66 and the clamp base 64 with the clamp arm 66 in a free position. In the free position, the flexible implant 12 is free to slide between the clamp base 64 and the clamp arm 66. The tensioning screw 56 is rotated until the receiver 62 is adjacent the implant housing 30 and the head 57 is adjacent the tensioning body 52.

When the head 57 of the tensioning screw 56 is adjacent the tensioning body 52, the ends of the flexible implant 12 are held or partially tensioned as the clamp arm 66 is moved to the clamped position as shown in FIG. 24. In the clamped position, the implant engagement portion 67 captures the flexible implant between the clamp arm 66 and the clamp base 64 to prevent the flexible implant 12 from moving relative to the implant housing 30. With the clamp arm 66 is the clamped position, the tensioning screw 56 is rotated within the tensioning body 52 to move the clamping mechanism 60 away from the implant housing 30 as shown in FIG. 25. The tensioning disc 58 of the tensioning screw 56 is fixed relative to the receiver 62 to move the receiver 62 away from the implant housing 30. As the receiver 62 moves away from the implant housing 30, the clamp base 64 moves away from the implant housing to tension the flexible implant 12 that is captured by clamp arm 66 and fixed relative to the clamp base 64. When the flexible implant 12 is tensioned, the implant set screw 37 may be tightened to fix the flexible implant 12 relative to the implant housing 30. When the flexible implant 12 is fixed to the implant housing 30, the tensioning instrument 50 may be removed from the implant housing 30.

The tensioning instrument 50 may be removed by trimming the excess portion of the flexible implant 12 as detailed above and removing the excess portion of the flexible implant 12 with the tensioning instrument 50. It will be appreciated, that the tensioning instrument 50 would retain the excess portion of the flexible implant 12. The tensioning instrument 50 may also be removed by releasing the flexible implant 12 by returning the clamp arm to the free position before trimming the excess portion of the flexible implant 12. The excess portion of the flexible implant 12 may include the leader 16.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. A method for securing a spinal rod to a bony element, the method comprising:

looping a flexible member around the bony element;

positioning the spinal rod in a first passage of a monolithic implant;

advancing a first screw in a first opening of the implant to secure the rod to the implant;

passing a portion of the flexible member through a second passage of the implant;

tensioning the flexible member about the bony element; and advancing a second screw in a second opening of the implant to secure the portion of the flexible member to the implant, the second opening being parallel to and offset from the first opening, wherein advancing the second screw comprises moving a chock engaged with the second screw into engagement with the flexible member and rotating the chock about a pin inserted through a housing of the implant and through the chock.

2. The method of claim 1, further comprising trimming an excess portion of the flexible member after advancing the second screw to secure the portion of the flexible member to the implant.

3. The method of claim 1, wherein tensioning the flexible member about the bony element and advancing the second screw to secure the portion of the flexible member to the implant occurs prior to advancing the first screw to secure the rod to the implant.

4. The method of claim 1, wherein looping a flexible member around the bony element includes passing a leader of the flexible member around the bony element and pulling the leader to draw the flexible member around the bony element.

5. The method of claim 1, wherein tensioning the flexible member includes engaging a tensioning instrument to the flexible member and to the implant.

6. The method of claim 5, wherein the tensioning instrument includes a clamping mechanism having an engagement portion and tensioning the flexible member includes clamping a portion of the flexible member within the engagement portion.

7. The method of claim 6, wherein tensioning the flexible member includes moving the clamping mechanism of the tensioning instrument while the flexible member is clamped within the clamping mechanism.

8. The method of claim 5, wherein tensioning the flexible member includes rotating a tensioning screw of the tensioning instrument to tension the flexible member.

9. The method of claim 1, wherein passing a portion of the flexible member through the second passage includes passing the portion of the flexible member in a direction transverse to the rod.

10. A method for securing a spinal rod to a bony element, the method comprising:

looping a flexible member around the bony element;

positioning the spinal rod in a first passage of a housing of an implant;

fixing the implant housing relative to the spinal rod;

passing a portion of the flexible member through a second passage of the implant housing;

rotating a chock about a pin inserted through the implant housing and through the chock to secure the flexible member relative to the implant housing.

11. The method of claim 10, wherein rotating the chock comprises advancing a screw in an opening of the implant housing, the screw being engaged with the chock.

12. The method of claim 10, further comprising tensioning the flexible member about the bony element.

13. The method of claim 12, wherein tensioning the flexible member about the bony element and rotating the chock about the pin to secure the flexible member relative to the implant housing occurs prior to fixing the implant housing relative to the spinal rod.

14. The method of claim 12, wherein tensioning the flexible member includes engaging a tensioning instrument to the flexible member and to the implant housing.

15. The method of claim 10, wherein passing a portion of the flexible member through the second passage includes passing the portion of the flexible member in a direction transverse to the rod.

16. A method for securing a spinal rod to a bony element, the method comprising:

looping a flexible member around the bony element;

positioning the spinal rod in a first passage of a monolithic implant;

passing a portion of the flexible member through a second passage of an implant housing;

advancing a screw into an opening of the implant to secure the portion of the flexible member to the implant;

rotating a chock about a pin inserted through a housing of the implant and through the chock;

tensioning the flexible member about the bony element by engaging the implant housing with a tensioning instrument and rotating a tensioning screw of the tensioning instrument.

17. The method of claim 16, further comprising advancing a rod set screw into a rod opening of the implant to secure the rod to the implant.

18. The method of claim 16, wherein tensioning the flexible member includes inserting a portion of the tensioning instrument within the implant housing.

19. The method of claim 16, wherein the rotating step moves the chock into engagement with the flexible member.

* * * * *